United States Patent [19]

Ekström et al.

[11] Patent Number: 5,663,790

[45] Date of Patent: Sep. 2, 1997

[54] METHOD AND APPARATUS FOR DETERMINATION OF REFRACTIVE INDEX

[75] Inventors: Björn Ekström, Upsala; Magnus Öberg, Hägersten, both of Sweden

[73] Assignee: Pharmacia Biosensor AB, Upsala, Sweden

[21] Appl. No.: 532,546

[22] PCT Filed: Apr. 8, 1994

[86] PCT No.: PCT/SE94/00312

§ 371 Date: Oct. 6, 1995

§ 102(e) Date: Oct. 6, 1995

[87] PCT Pub. No.: WO94/24542

PCT Pub. Date: Oct. 27, 1994

[30] Foreign Application Priority Data

Apr. 8, 1993 [SE] Sweden ................. 9301192

[51] Int. Cl.⁶ ........................... G01N 21/41
[52] U.S. Cl. ............. 356/128; 356/133; 356/361
[58] Field of Search ............... 356/128, 133, 356/73.1, 361, 345; 385/12, 43; 250/227.14, 227.19, 227.21, 227.25, 227.27, 227.28

[56] References Cited

U.S. PATENT DOCUMENTS

| 4,240,747 | 12/1980 | Harmer | 356/133 |
| 4,950,074 | 8/1990 | Fabricius et al. | 356/133 |
| 5,173,747 | 12/1992 | Boiarski et al. | 356/128 |
| 5,377,008 | 12/1994 | Ridgway et al. | 356/128 |

FOREIGN PATENT DOCUMENTS

| 0340577 | 11/1989 | European Pat. Off. . |
| WO88/10418 | 12/1988 | WIPO . |
| WO91/03728 | 3/1991 | WIPO . |

Primary Examiner—Hoa Q. Pham
Attorney, Agent, or Firm—Birch, Stewart, Kolasch & Birch, LLP

[57] ABSTRACT

In a method of determining the refractive index of a gaseous, liquid or solid sample, preferably a gaseous or liquid sample, there is used a waveguide resonator (1) which includes an open waveguide (4) and a closed waveguide (5) located adjacent the open waveguide. The sample is brought to the vicinity of the closed waveguide (5) so as to influence the proximal surroundings of the waveguide and therewith its effective refractive index. Light derived from a light source (9) is coupled to one end of the open waveguide (4) and transmitted light is measured at the other end of the open waveguide to establish the influence of the sample on the resonance wavelength and therewith determine the refractive index of the sample or a sample-related refractive index difference. A device for carrying out the method includes a waveguide resonator having a sample contact area (12) adjacent the closed waveguide (5) of the waveguide resonator.

71 Claims, 7 Drawing Sheets

METHOD AND APPARATUS FOR DETERMINATION OF REFRACTIVE INDEX

BACKGROUND OF THE INVENTION

The present invention relates to a novel method for determining refractive index, and to the use of this method in determining qualitatively or quantitatively the presence of a substance in a gaseous, liquid or solid sample. The invention also relates to a sensor device for carrying out the method.

In its simplest form, a ring resonator is comprised of an open (normally straight) optical waveguide which is located closely adjacent to a closed (normally annular or ring-shaped) optical waveguide. When light from a single-mode laser, i.e. a laser which transmits laser light of single wavelength, is coupled into the open waveguide, some of this light will also be coupled to the annular waveguide in the region where the two waveguides lie close together. Normally, the light concerned in this regard will constitute only one or some percent of the total light. However, if the wavelength of the laser light is such that the waveguide ring is able to accommodate precisely a whole number of wavelengths, the resonance conditions of the ring for this wavelength are fulfilled and substantially more light will be coupled to the ring and be stored therein, which, in turn, results in a corresponding reduction in the amount of light that is transmitted at the output end of the open waveguide. Thus, when seen over a range of wavelengths, the resonance will be observed at the output end of the open waveguide as a sharp minimum in the power of the transmitted light. This phenomenon has been utilized in rotary sensors, such as the gyro, among other things, and also to determine very low propagation losses in waveguides.

The resonance condition for a ring resonator can be written as:

$$2 \cdot \pi \cdot R \cdot n_{\text{eff}} = m \cdot \lambda$$

where R is the radius of the ring, $n_{\text{eff}}$ is the effective refractive index of the waveguide, m is an integer and $\lambda$ is the wavelength of the laser light. In order to be able to detect a resonance, it is necessary to vary the laser light wavelength $\lambda$ and to detect the effect upon the light coming from the open waveguide. It will be seen from the formula that when the effective refractive index $n_{\text{eff}}$ of the ring changes, the resonance wavelengths will also change. The effective refractive index ($n_{\text{eff}}$) is, in turn, influenced by all media in which the wave-guided light propagates, mostly in the actual core of the waveguide although also in materials closely surrounding the core.

WO 91/03728 describes the use of a waveguide based sensor system for determining the concentration of a chemical substance, wherein there is produced two mutually separate evanescent fields having mutually different penetration depths. According to one embodiment, the system includes a ring resonator and there is determined a relative absorption change in relation to the concentration of the chemical substance.

SUMMARY OF THE INVENTION

The present invention is based on the concept of utilizing the dependency of the resonance wavelength in a ring-resonator type sensor on the surroundings of the waveguide core to determine refractive index or changes in refractive index in a gas, liquid or solid material, by placing such a sample in the immediate vicinity of the waveguide core. More specifically, the proposed measuring method is based on applying the sample onto a sample surface essentially on top of the closed waveguide itself, i.e. in the case of a simple ring-resonator on top of the waveguide ring, the resonance wavelength $\lambda$ of the waveguide ring being changed in proportion to the change in refractive index that is occasioned by the sample.

The present invention thus enables the bulk refractive index to be determined in primarily liquids or gases, although possibly also in solid materials, both statically and in flow cells, for instance for analysis and monitoring purposes, such as in FIA, liquid chromatography, electrophoresis, gas and liquid assays in process controls, in vehicle contexts, and so on. Furthermore, the interactions of different species with a derivatized sample surface or a sample surface pretreated in some other way can be detected via the change in refractive index that is occasioned in the surface layer by the interaction. In this case, the ring resonator functions as a specific sensor (e.g. as a so-called biosensor).

One advantage of a sensor based on this ring-resonator principle is that it can be made relatively small and still have a long length of interaction with the sample solution, thereby enabling a highly responsive system to be achieved, this responsiveness, or sensitivity, being proportional to the number of wavelengths that are accommodated by the waveguide ring.

Thus, one aspect of the invention relates to a method of determining the refractive index of a gaseous, liquid or solid sample, preferably a gaseous or liquid sample, which is characterized by placing the sample adjacent to a closed waveguide of a waveguide resonator comprising an open waveguide and said closed waveguide located adjacent thereto, so as to influence the proximal surroundings of the closed waveguide and therewith its effective refractive index, coupling light from a light source into one end of the open waveguide and measuring transmitted light at the other end of said open waveguide, and establishing the influence of the sample on the resonance wavelength so as thereby to determine the refractive index of the sample or a sample-related refractive index difference.

According to another aspect, the invention relates to a device for determining the refractive index of a gaseous, liquid or solid sample, preferably a gaseous or liquid sample, wherein the device comprises a waveguide resonator which includes an open waveguide, a closed waveguide disposed adjacent the open waveguide, means for coupling light to one end of the open waveguide, means for detecting transmitted light at the other end of the open waveguide, a light source for emitting said light to the open waveguide, and a sample contact area disposed in connection with the closed waveguide of the waveguide resonator.

The term sample shall be interpreted in its widest meaning and relates generally to any liquid, gas or possibly solid material that shall be studied with the aid of the method or the device of the invention.

According to one preferred embodiment, a further waveguide resonator which is shielded from the surroundings is used as a reference, so that all changes in the refractive index of the sample will be detected as a relative wavelength shift between sample waveguide resonator and reference waveguide resonator. This avoids temperature influences and uncertainty concerning the wavelength of the light source.

As beforementioned, the open waveguide is most often straight or includes at least straight parts, although it may, of course, have some other configuration provided that the requisite waveguide function is maintained. The waveguide may also have one or more inputs and one or more outputs. Alternatively, an input may be branched into several parallel waveguide parts.

The closed waveguide is normally ring-shaped, i.e. circular, although it may have any other closed path shape, such as an elliptical shape or the shape of a "running track" for instance (i.e. a path having parallel straight center parts and circular curved ends). This latter shape provides a somewhat greater coupling (longer "coupling path") than a circular ring, when the straight parts of the path are placed parallel with a straight, open waveguide. It can be said generally that the coupling path between the open and closed waveguides is adjusted/lengthened by causing the open and closed waveguides to extend parallel with one another over some given distance. In the case of a path that has the shape of a running track, the coupling distance can be adjusted, and possibly lengthened still further, by varying the length of the straight parts of the path.

However, the closed waveguide may alternatively have the form of a linear resonator, for instance of the Fabry-Perot type having mirrors provided at each end, or of the Bragg type which includes a reflective grating placed transversely across at least the ends of a linear waveguide, so that a standing resonance wave can be generated in the waveguide. Instead of parallel, straight parts, the open and closed waveguides may include parallel, curved parts, for instance two parallel circle-arcs (such as a circular-arcuate part of an open waveguide placed adjacent a circular, closed waveguide).

When determining in accordance with the invention an absolute or relative resonance wavelength shift caused by the sample, and determining the sample refractive index or difference in refractive index relative to a reference on the basis of this shift, the light source used may be a broadband light source (polychromatic light source) such as, e.g., a xenon lamp or deuterium lamp or a light emitting diode (LED), wherein the light is divided spectrally prior to detection, suitably on the output side, with the aid of a grating or a prism.

However, in the case of this variant there is preferably used a light source of variable (sweepable) wavelength, such as a laser of tunable wavelength. In this case, the spectral width of the coupled light shall be at least in the same order of magnitude as, and preferably significantly smaller than the width of the resonance dip or dips that is, or are, detected when sweeping the light wavelength.

Furthermore, with regard to the light wavelength the detection sensitivity of the waveguide resonator will increase with decreasing wavelengths, although the penetration depth in the sample contact area will decrease at the same time. It should also be mentioned in this context that when guiding waves optically, the optical field will decay exponentially outside the waveguide core (provided that all surrounding layers have a refractive index which is lower than the refractive index of the waveguide core). As will readily be understood, the intermediate layer between sample and the closed measuring waveguide should therefore be as thin as possible, or possibly not be included at all, so as to achieve maximum penetration of the sample.

Although the waveguide structures may be of a multiple mode type, single-mode waveguide structures are preferred, i.e. waveguide structures in which only one beam path (only one type of optical field image) can be propagated.

BRIEF DESCRIPTION OF THE DRAWINGS

The invention will now be described in more detail with regard to particular, non-limiting embodiments thereof, reference being made to the accompanying drawings, in which.

DETAILED DESCRIPTION OF THE INVENTION

Figure 1:
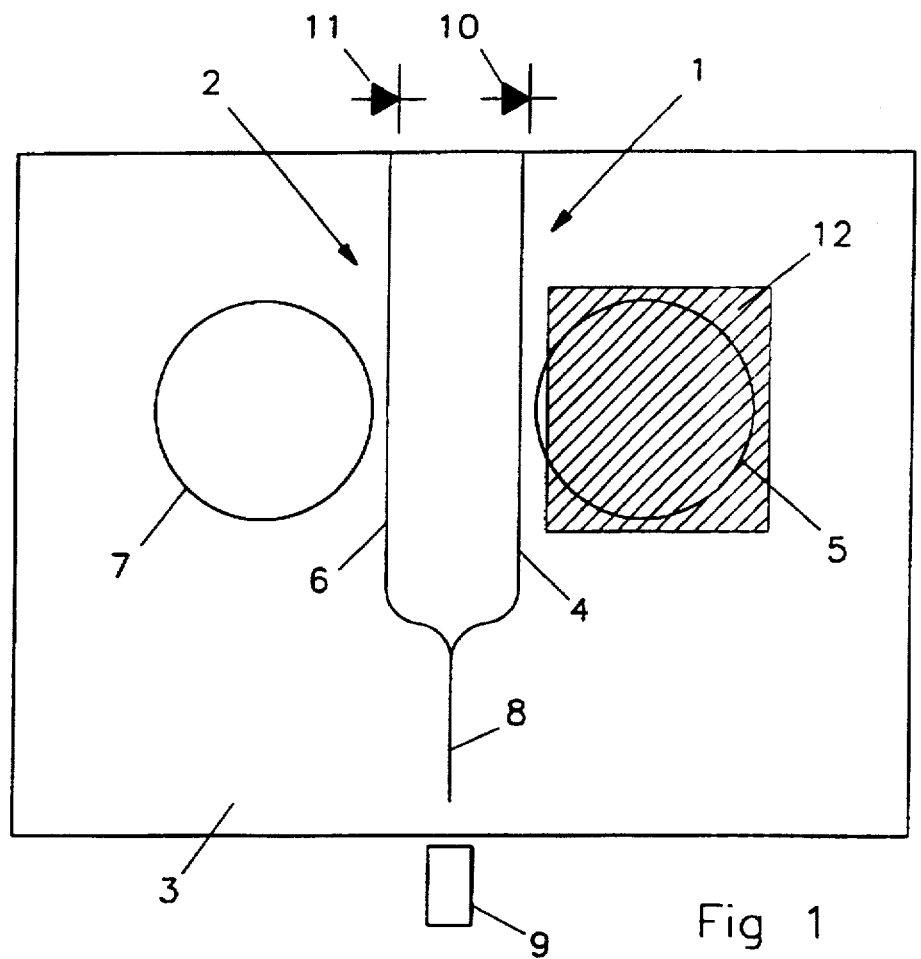
FIG. 1 illustrates schematically a ring resonator sensor according to the invention having a measuring ring resonator arm and a reference ring resonator arm.

The main components of the ring resonator based sensor illustrated in FIG. 1 are a measuring ring resonator arm 1 and a reference ring resonator arm 2, both of which are formed on a silicon chip 3. The measuring ring resonator arm 1 is comprised of a straight waveguide 4 and a ring-shaped waveguide 5, in a known manner. Correspondingly, the reference ring resonator arm 2 is comprised of a straight waveguide 6 and a ring-shaped waveguide 7. The two straight waveguides 4, 6 branch-out at one end from a common straight waveguide-part 8 which is arranged for coupling of light from a laser 9 of continuously tunable wavelength. A measuring detector 10 and a reference detector 11 are provided at the other ends of respective straight waveguides 4, 6. A sample region or area 12 is formed over the ring-shaped waveguide 5 of the measuring ring resonator 1.

Figure 2:
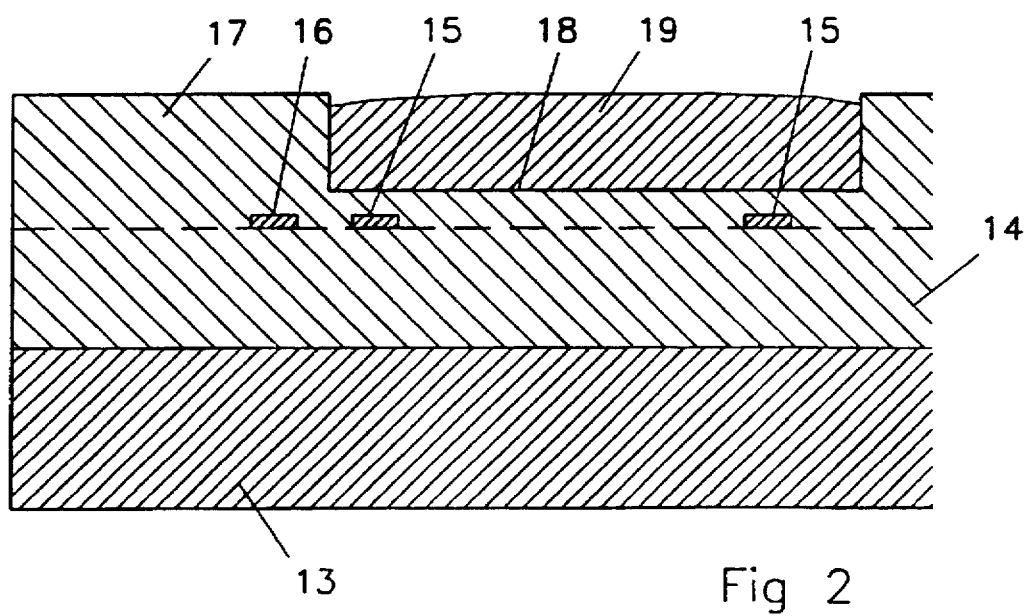
FIG. 2 is a schematic section view of one embodiment of a measuring ring resonator.

A more detailed example of how a measuring ring resonator (not coupled to a reference ring resonator in this case) may be arranged is shown schematically in FIG. 2. A layer of thermic silicon dioxide 14 which supports a straight waveguide 16 (corresponding to the straight waveguide 4 in FIG. 1) and a ring-shaped waveguide 15 (corresponding to the ring-shaped waveguide 5 in FIG. 1) formed from silicon nitride is applied to an underlying silicon substrate 13. The waveguides 15, 16 are surrounded by a silicon dioxide layer 17. A sample region or area 18 (corresponding to the sample region or area 12 in FIG. 1) is recessed in this layer, above the ring-shaped waveguide 15. In the illustrated case, the sample recess is filled with a sample 19 in a manner such as to leave only a thin oxide layer over the ring 15. In the case of a sensor which also includes a reference ring resonator, this latter resonator will, of course, be constructed in a similar way, except that the sample region 18 is omitted. As the person skilled in this art will be aware, very small dimensions and thin layers are normally concerned, as will also be apparent from the exemplifying embodiments described here below.

In order to complete a ring resonator sensor with the aforedescribed sensor chip, it can be arranged as in FIG. 1 that the light from a laser, for instance a diode laser whose wavelength can be varied continuously with a control current (so-called DBR-laser, where DBR stands for Distributed Bragg Reflector), can be coupled to the input end of the ring resonator chip via an optic isolator, a fiber and a polarization rotator (not shown). The light on the output side is coupled to a measuring detector and to a reference detector (corresponding to the detector 10, 11 in FIG. 1), respectively, via further fibers (not shown).

Referring again to FIG. 1, when light of a single wavelength is coupled from the diode laser 9 to the input end of the ring resonator chip, some of the laser light in the straight waveguides 4, 6 will be coupled to the ring-shaped waveguides 5, 7, in accordance with what was said in the introduction with regard to ring resonators. As already mentioned in the aforegoing, when the wavelength of the laser light is varied continuously, the resonance condition for the waveguide rings will be fulfilled at certain wavelengths, i.e. a whole number of wavelengths will be accommodated precisely in the rings. Consequently, at these wavelengths substantially more light will be coupled to the rings and be stored therein, which when detecting the light at the output end of the sensor chip will manifest itself as sharp minima in the transmitted light effect. As will be seen from the resonance condition formula given in the introduction, the positions of the resonances is determined by the size of the rings (the radius R) and by the effective refractive index ($n_{eff}$) of the waveguides, which in turn is influenced by all media in which the wave-guided light is present, mostly by the waveguide core itself but also by the nearest surrounding materials.

Figure 3:
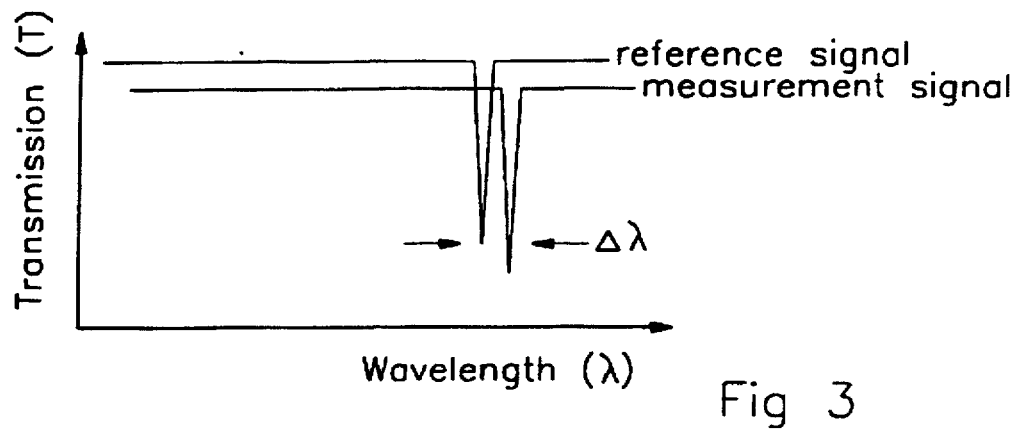
FIG. 3 is a diagrammatic illustration of a ring resonator sensor according to FIG. 1 and shows transmission at the end of the straight waveguide as a function of the laser light wavelength for both measuring signal and reference signal.

When a sample is applied on top of the measuring ring 5 in the sample region 12 (the sample recess 18 in FIG. 2), the wavelengths of these minima will thus differ between the measuring ring resonator 1 and the reference ring resonator 2. This is illustrated in a somewhat simplified manner in FIG. 3, which illustrates the resultant shift (wavelength difference), designated $\Delta\lambda$, between a pair of minima for the measuring signal and the reference signal. In the present case, for the sake of simplicity these minima are assumed to lie at the same wavelength prior to applying the sample. In reality the two minima are slightly displaced relative to one another even at this stage, because the respective nearest surroundings are not identical. It will readily be understood that the illustrated minimum for each ring is only one of a large number of essentially equidistant resonances that are obtained when sweeping the wavelength. The wavelength shift $\Delta\lambda$ is representative of the difference in the refractive index between the surroundings of the reference ring 7 and the measuring ring 5, and is therewith related to the refractive index of the sample. In this way, when the sample is a liquid it is possible to detect small quantities of additive substances in the liquid which give rise to refractive index differences.

It will be understood that it is possible to omit the reference ring resonator from the sensor chip and, instead, determine wavelength shifts for solely the measuring ring resonator. The use of a reference ring resonator is preferred, however, since this will avoid the influence of temperature and uncertainty in laser wavelength.

Liquid samples can be measured with the aid of the ring resonator sensor, principally by bringing a sample solution and a reference solution into contact with the sample region above the measuring ring. The differences in the refractive index between the two solutions can then be determined by either (i) absolute measurement in the absence of the reference ring resonator, by measuring the change in resonance wavelength in the measuring ring resonator for the two cases, or (ii) relative measurement with the aid of the reference ring resonator, by measuring the difference in refractive index between measuring ring resonator and reference ring resonator in these two cases, and then using the difference between said two cases as a measurement of the difference between the refractive indexes of the two solutions.

It is necessary to know the wavelength of the laser light at each moment, in order to be able to calibrate the measuring method. A simple method of calibrating the wavelength sweep is to make the reference ring so large that a plurality of resonances will be passed during a normal sweep. This enables any non-linearities in the current-wavelength characteristic of the laser to be compensated-out, since the resonance positions of the reference ring are well defined. In other words, a measured wavelength shift can be corrected for variations in the ideally linear dependency of the wavelength on the laser current. This enables very large refractive index differences to be determined with a high degree of accuracy, wherewith the measuring principle will obtain a very large dynamic range.

Naturally, in order to achieve maximum response or sensitivity it is necessary for the effective refractive index ($n_{eff}$ in the aforesaid formula) to change as much as possible with a varying sample index, i.e. $d(n_{eff})/d(n_{sample})$ shall be as large as possible. The thinner the layer between the sample and the waveguide, the greater the increase in $d(n_{eff})/d(n_{sample})$ for given materials. It has been found in practice, however, that an excessively thin layer can result in an increase in waveguide losses in the ring, and therewith in undesirable blurred resonances.

The magnitude of those wavelength shifts that can be detected are determined by the sharpness of the resonance minima, i.e. the half-width. The smaller the half-widths, the smaller the wavelength shifts that can be detected. Sharp minima are generally obtained for a high so-called Q-value in the ring-shaped waveguide, i.e. for low waveguide losses, a large ring and a low degree of light-coupling to the straight waveguide.

For example, if it is assumed that it is possible to obtain resonance minima with a half-width of say 0.11 Å (which is a quite reasonable assumption against the background of the tests that have been carried out hitherto), a change in the refraction index of the sample of $1.3 \times 10^{-4}$ would result in a wavelength shift of a full half-width. It should be possible to detect roughly one hundredth of this wavelength shift by analyzing the curve form of the whole of the minima, and therewith enable a refractive index change of $1.3 \times 10^{-6}$ to be detected. When the sample is comprised of bovine serum albumin (BSA) for instance, this would correspond to a concentration change of about 0.8 µg/ml.

It has been found that irregularities in or roughness of the sample surface in the proximity of the waveguide core is able to cause unsharpness or blurring in the resonances as a result of increased dispersion losses. This problem can be resolved, by using a sample vehicle that has an appropriate refractive index, so as to essentially erase differences in the refractive index at the interface between the covering oxide and sample. A method of providing a uniform and smooth sample surface instead will be described further on.

As indicated in the aforegoing, the aforedescribed ring resonator sensor can be used to determine the bulk refractive index of a liquid or a gas that has been applied to the sample region (the recess 18 in FIG. 2). This can be achieved, for instance, by configuring the chip as a "dipstick" or probe and placing the chip in the sample or in a sample flow. Alternatively, there can be provided a sample container for stationary samples or a throughflow cell in direct connection with the sample area above the sample ring.

Figure 4:
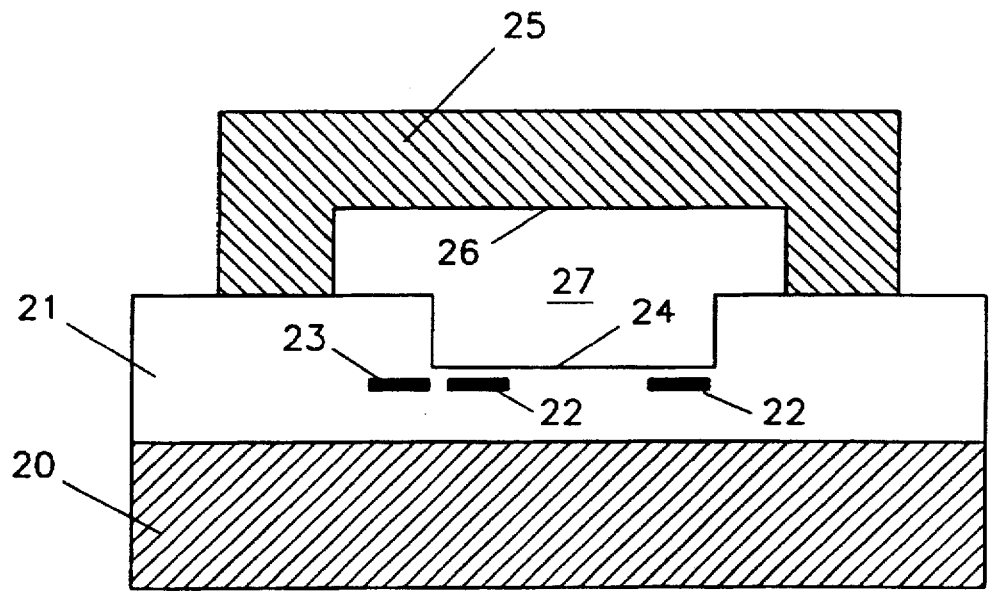
FIG. 4 is a sectional view of an example of a flow cell integrated with a ring resonator sensor.

FIG. 4 illustrates one example of a ring resonator sensor combined with a flow cell. As in the earlier case, the ring resonator sensor itself is comprised of a silicon chip 20 having a silicon oxide layer 21 which contains a ring resonator 22, a straight waveguide 23 and a sample recess 24. An upper flat element 25, which in the present case includes a recess 26 which faces towards the silicon chip 20, is attached to the upper side of the chip and defines a flow channel 27 together with the sample recess 24.

As indicated in the aforegoing, it may also be possible to determine the refractive index of a solid material that is pressed against the sample area of the sensor, via an immersion oil or like substance when required. It is thought that this principle method of measuring bulk refractive index can be used generally for at least the majority of applications that are at present based on or are intended to be based on measuring the bulk refractive index. Examples of such applications are FIA (Flow Injection Analysis), liquid chromatography, electrophoresis (both capillary electrophoresis and slab electrophoresis), gas and liquid measuring processes within the field of process control and in automotive vehicle contexts.

Figure 5A:
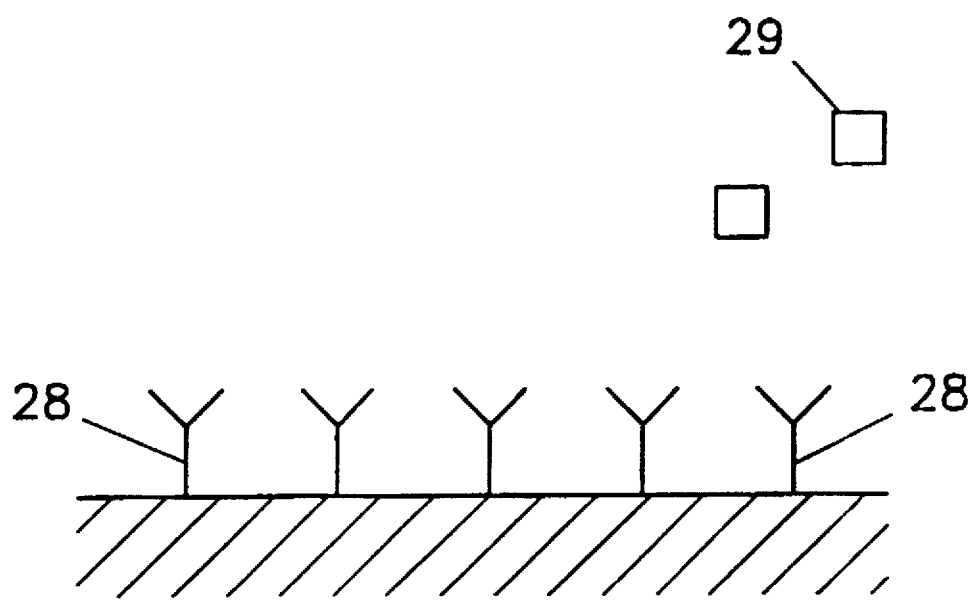
FIGS. 5A and 5B are schematic illustrations of a measuring surface with an immobilized antibody in contact with an analyte-containing sample solution.
Figure 5B:
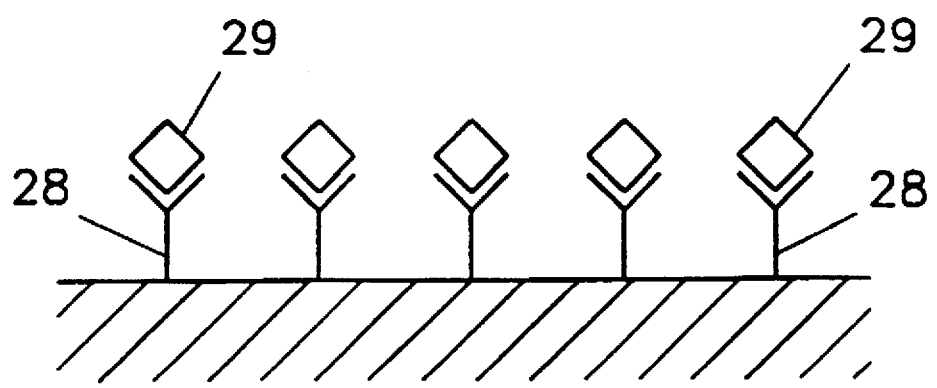

The ring resonator sensor can also be used for surface interaction detection. In this case, the sample area of the ring resonator is provided, for instance by derivatization, with a surface layer which interacts specifically or group-specifically with molecules in a sample which is brought into contact with the surface. When biomolecules are involved, the ring resonator will thus function as a so-called biosensor. For instance, different immunoassays and hybridization assays (DNA and RNA interactions) can advantageously be performed with a ring resonator that has been prepared in this way. One example of this is illustrated schematically in FIG. 5A, which shows the sample surface above the waveguide ring provided with immobilized antibodies 28 directed specifically against an analyte 29 in an applied liquid sample in contact with the sample surface. When the analyte molecules 29 bind to the antibodies 28, as illustrated in FIG. 5B, the sample surface is changed, which is manifested as a detectable resonance shift. The magnitude of this resonance shift is governed by the amount of analyte that binds to the surface and also by the size of the analyte.

As will be readily understood, large molecules, e.g. a biomacromolecule, such as a protein molecule, will result in larger changes in refractive index than a smaller molecule, for instance a hapten.

In certain respects, this surface interaction application can be said to have large similarities with the biosensor technique based on surface plasmon resonance (SPR) described in the literature and also commercially available (BIAcore™, Pharmacia Biosensor AB, Uppsala, Sweden).

Since the SPR-technique also involves a form of refractive index measuring technique, it should be possible to use a ring resonator sensor according to the invention in conjunction with those applications that have been described with reference to the SPR-technique, and also in certain cases the preparation of sensing surfaces, the configuration of measuring cells and the handling of liquids described with regard to said technique. Reference can be made in this respect to the teachings of, for example, WO 90/05295, WO 90/05303 and WO 90/05305. Different methods of increasing the measurement signal in SPR-assays, by amplifying the detected change in optical density at the surface interactions concerned, and which may also be applied in the present context, are described in EP-A-276 142 for instance. Dipstick variants and throughflow variants of the ring resonator sensor are also conceivable generally for such surface interaction measurements. It is conceivable that the surface measuring principle can also be applied within several other fields in addition to bioanalysis, for instance in the field of gas sensors.

The described ring resonator sensor can be modified so that with the aid of a multiple arrangement it is possible to measure several different specificities on different surface elements of a sensor wafer having different functionalities and located in the close proximity of one another. For instance, it is conceivable to arrange several ring resonators in cascade so as to obtain several different sample surfaces or sample channels with one and the same signal laser and one or more reference rings.

Figure 6:
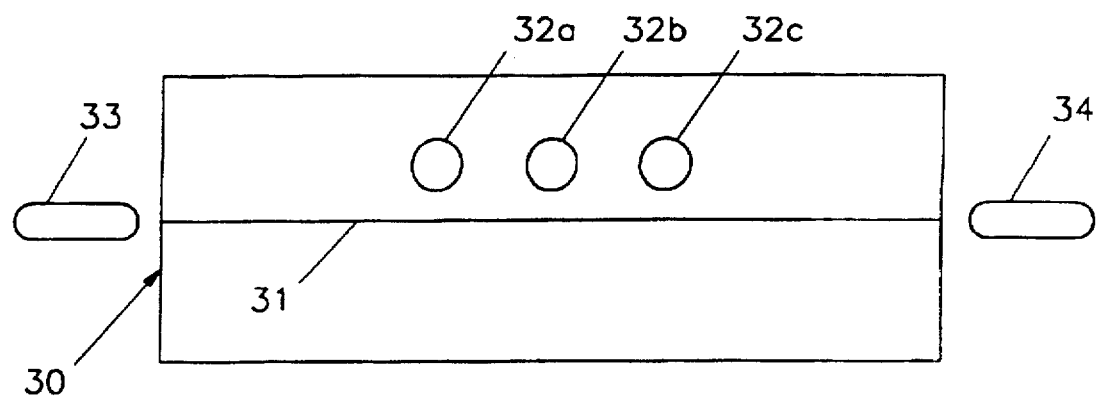
FIG. 6 is a schematic illustration of series connected ring resonators.

FIG. 6 illustrates an example of such a cascade array. The sensor chip, here referenced generally 30, has an open, straight waveguide 31 along which three ring-shaped waveguides 32a, 32b and 32c are sequentially arranged. Sample contact surfaces are arranged over two of these waveguides, for instance the rings 32a and 32b (not shown), wherein the third ring 32c functions as a reference ring. In order to be able to function independently of one another, the serially arranged rings shall have different diameters so as to produce different resonance wavelengths. The input to the open waveguide 31 is connected to a light source 33 (for instance a laser), while the output is connected to a photodetector 34.

In the case of the illustrated series-coupling of three rings, shown by way of example, it is possible to assay two different components (analytes) of a sample simultaneously, when the respective sample contact areas exhibit corresponding functional specificities. Naturally, a series coupling which includes more rings will enable several analytes to be assayed simultaneously.

Figure 7:
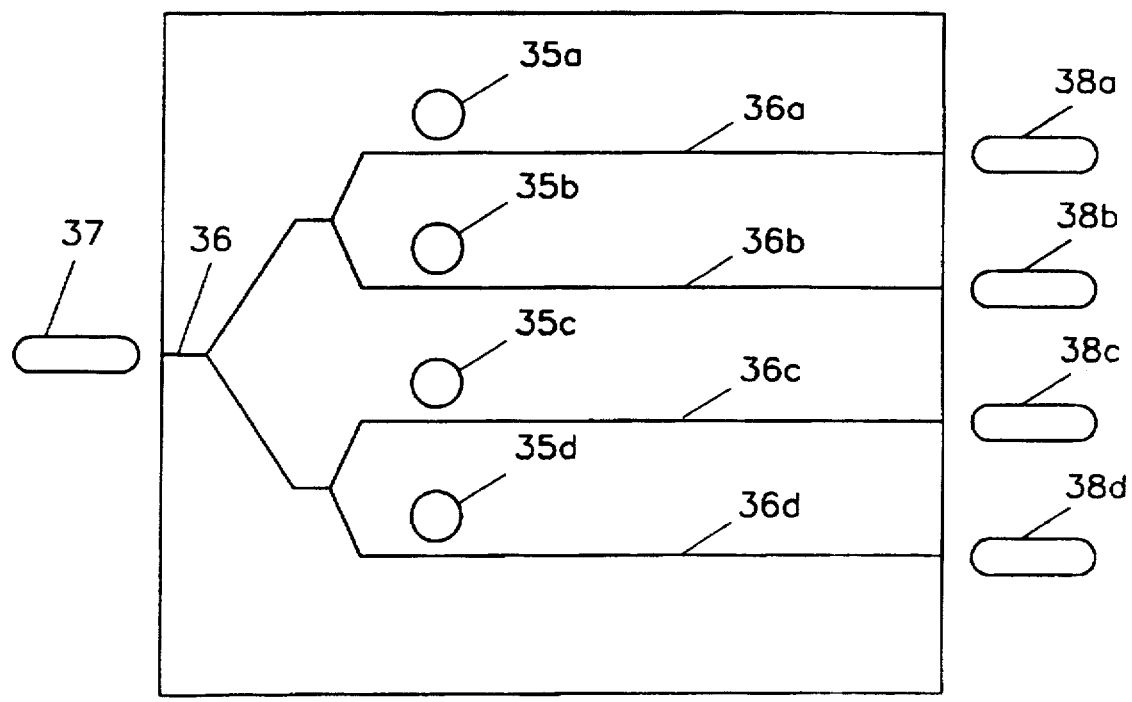
FIG. 7 is a schematic illustration of ring resonators connected in parallel.

FIG. 7 illustrates an example of an arrangement which includes parallel measuring ring resonators. In the illustrated case, four rings 35a–d are arranged mutually in parallel adjacent a respective straight waveguide part 36a–d which branches from a common waveguide part 36, to which light from a light source 37 is coupled (for instance from a laser, as in the aforegoing). The outputs of respective waveguide parts 36a–d are each connected to a respective photodetector 38a–d. For instance, the rings 35a–c may be provided with sample contact areas (not shown) wherein the ring 35d is allowed to function as a reference ring resonator together with the waveguide part 36d. For instance, such a parallel-coupled ring resonator system can be used for monitoring several (in this case three) electrophoresis paths simultaneously.

A silicon-based sensor chip of the type described above with reference to FIGS. 1, 2, 4 and 6 can be manufactured in the following manner:

One or more silicon plates are oxidized thermally so as to obtain a silicon dioxide layer, for instance a layer in the order of about 5 µm. A thin silicon nitride layer, for instance in the order of about 1200 Å, is then applied by plasma deposition, this layer forming the actual waveguide cores in the desired waveguide structures. After patterning the structures, the structures are etched-out by nitride etching. A phosphorus-doped LTO-oxide is then deposited to form an upper cover and protective layer for the respective waveguide structures. This LTO-oxide layer on top of the measuring waveguide rings is then etched down so that only a thin layer remains in the bottoms of respective sample contact recesses. The entire system is then baked at an appropriate temperature, for instance at a temperature of about 1100° C. The silicon plate or plates is/are finally cut into individual sensor chips.

The LTO-oxide deposition process is suitably effected in two stages, wherein the oxide is brought to a desired thickness on the measuring ring or rings (typically a thickness of 0–500 nm) in the first stage, and a relatively thick isolating layer (normally greater than 1.5 µm) is formed in the second stage, this isolating layer being intended to isolate all remaining waveguides from the surroundings. This second layer can then be etched down completely above the measuring ring or rings.

Alternatively, in this latter case the upper, thicker LTO-oxide layer may be replaced with a patternable silicone rubber or like substance. This enables the critical step of isotropic down-etching of the LTO-oxide layer on top of the measuring ring structures, which tends to produce a disturbing, rough surface, to be replaced with a simple lithographic patterning and development process. Furthermore, the not unimportant advantage is achieved whereby the silicone rubber can given a thickness (e.g. in the order of 10–30 µm) sufficient to enable the formation of flow channels which form measuring cells directly on the sensor chip. When such a silicone rubber layer is applied instead of the thick LTO-oxide layer, the silicon plate or plates is/are first baked at a temperature of 1100° C. after depositing the thin LTO-oxide layer. This LTO-oxide layer may optionally be omitted completely. The silicone rubber is then patterned in a conventional way, using masking fitters and then developed, whereafter the silicon plate or plates is/are cut into individual chips as described above.

The invention will now be described in more detail with reference to a number of non-limiting exemplifying embodiments thereof.

EXAMPLE 1

Production of a Ring Resonator Chip

A silicon substrate having a diameter of 10 cm was oxidized thermally to a silicon dioxide thickness of about 5 µm. Silicon nitride was then plasma deposited to a thickness of about 1400 Å and the waveguide structures were patterned on the silicon nitride layer and the individual straight and ring-shaped waveguides respectively were etched from the silicon nitride layer by means of a nitride etching process, the ring-shaped waveguides having radii of 1000 µm. A phosphorus-doped (4%) LTO-oxide layer was then deposited in one or two steps, whereafter the sample regions on top of the sample waveguide rings were patterned and etched down to 0.4 µm. After being baked at 1000° C., the silicon plates were finally cut into individual sensor chips each measuring 6×20 mm. The smallest distance between the waveguide ring and the straight waveguide was 1 µm and the waveguide width was about 5 µm.

For the purpose of optically evaluating the manufactured ring resonator chips the light source used was a semiconductor DBR-laser of tunable wavelength and of local manufacture (Öberg, M., et al., IEEE Photon Technol. Lett., Vol. 4, No. 3, March 1992, pages 230–232), measuring 800×400 µm, and having a wavelength of 1550 nm and a sweep range (wavelength modulation) of 1–1.5 nm. The laser light was coupled to the input end of a ring resonator chip via an optical isolator, an optical fiber and a polarization rotator. On the output side of the resonator chip the light was coupled to a detector (germanium photodiode) via a further optical fiber. The waveguide loss was calculated to be about 1 dB/cm and the degree of light coupling between the ring and the straight waveguide was from 5 to 15%.

Determination of the Refractive Index of a Sample Solution

Figure 8:
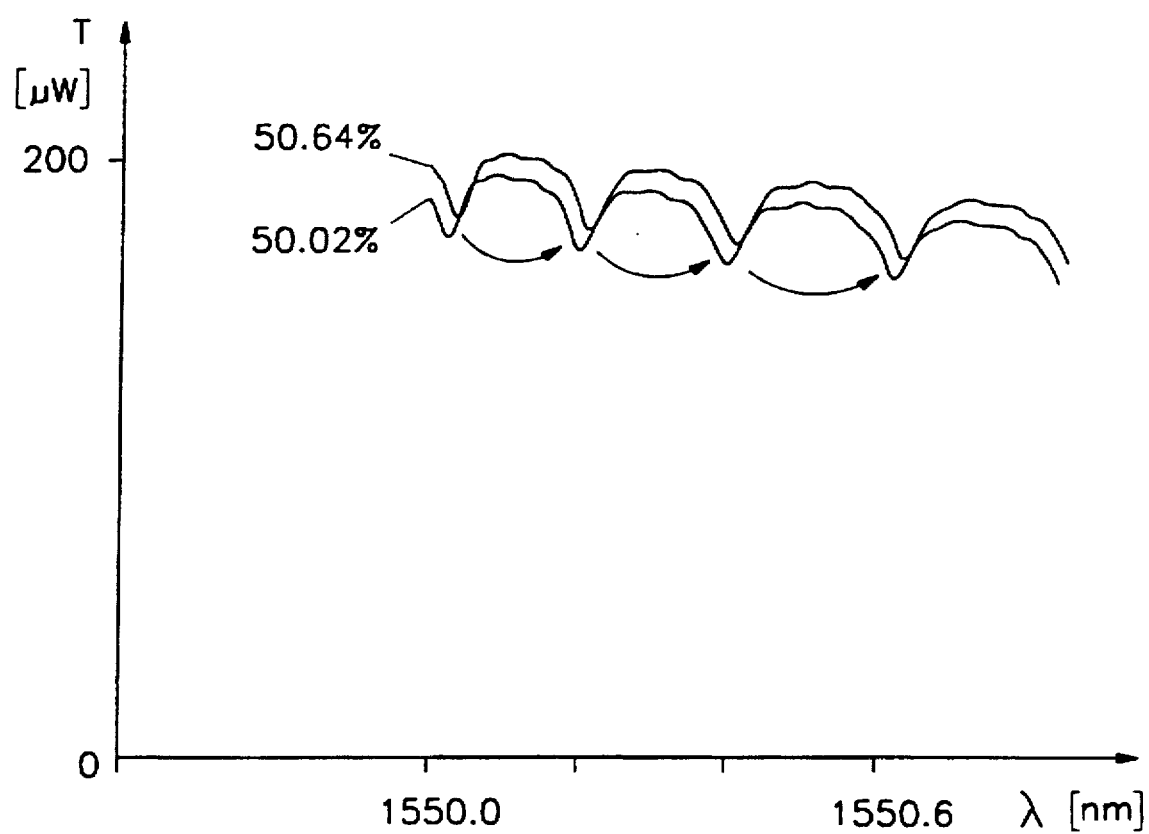
FIG. 8 is a diagram which illustrates for a ring resonator sensor according to FIG. 2 (i.e. in the absence of a reference ring resonator) the transmission at the end of the straight waveguide as a function of the laser light wavelength of a sugar solution sample with two different sugar concentrations.

The manner in which the ring resonator reacted to different sugar solutions was investigated with the aid of a ring resonator chip produced and coupled in the aforedescribed manner. The sugar solutions were applied to the sample surface on top of the upper surface of the ring-shaped waveguide with the aid of a specially manufactured docking cell. FIG. 8 illustrates the transmission curve for a change from 50.02% to 50.64% sugar. This change corresponds to a change of refractive index of $1.3 \times 10^{-3}$, which gave a clear resonance shift of almost one full period (more precisely 0.9 of a period) or about 2.0 Å as shown in the Figure.

EXAMPLE 2

Figure 9A:
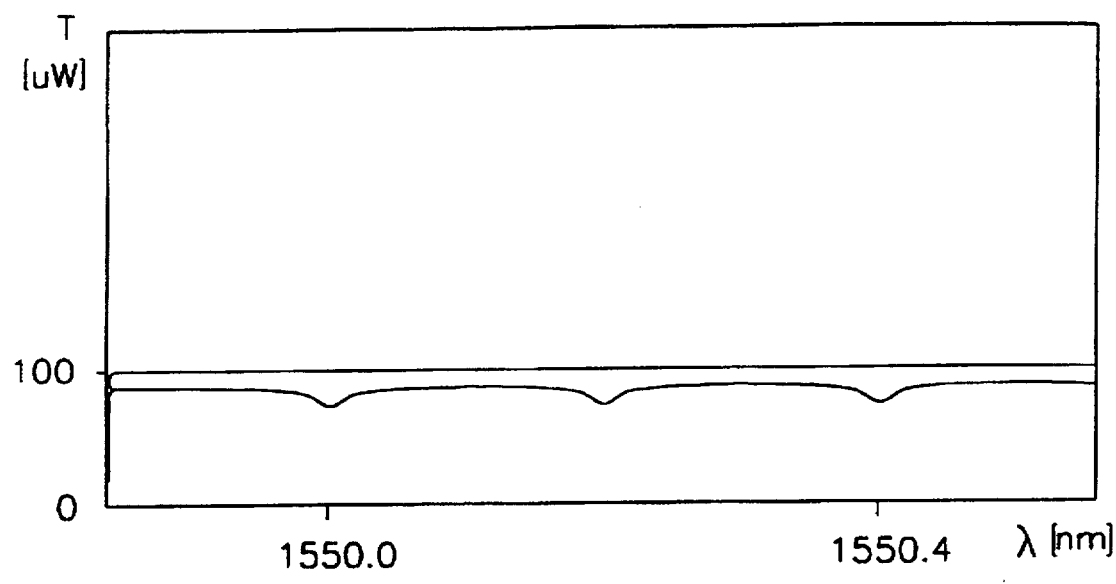
FIGS. 9A and 9B are diagrams which for a ring resonator sensor according to FIG. 1 (i.e. with a reference ring resonator) each show transmission curves for a sample ring resonator and a reference ring resonator, respectively, wherein the sample surface respectively includes and lacks a silicone rubber coating.

A sensor chip having a ring resonator system according to FIG. 1 was manufactured in the same way as that described in Example 1 above. After coupling the sensor chip to a laser and photodetectors as in the case of Example 1 (although in this case two detectors were used, one measuring detector and one reference detector) transmission curves were produced for the measuring and the reference ring resonator, respectively, with solely air on the sample region of the measuring ring. The result is shown in FIG. 9A, with the measuring detector curve uppermost and the reference detector curve lowermost. Although resonances were obtained in the reference detector curve, no resonances were noted in the measuring detector curve, which indicates that the thin LTO-oxide layer on top of the measuring ring is not sufficient to complete a waveguiding construction with the measuring ring and the underlying silicon substrate.

Figure 9B:
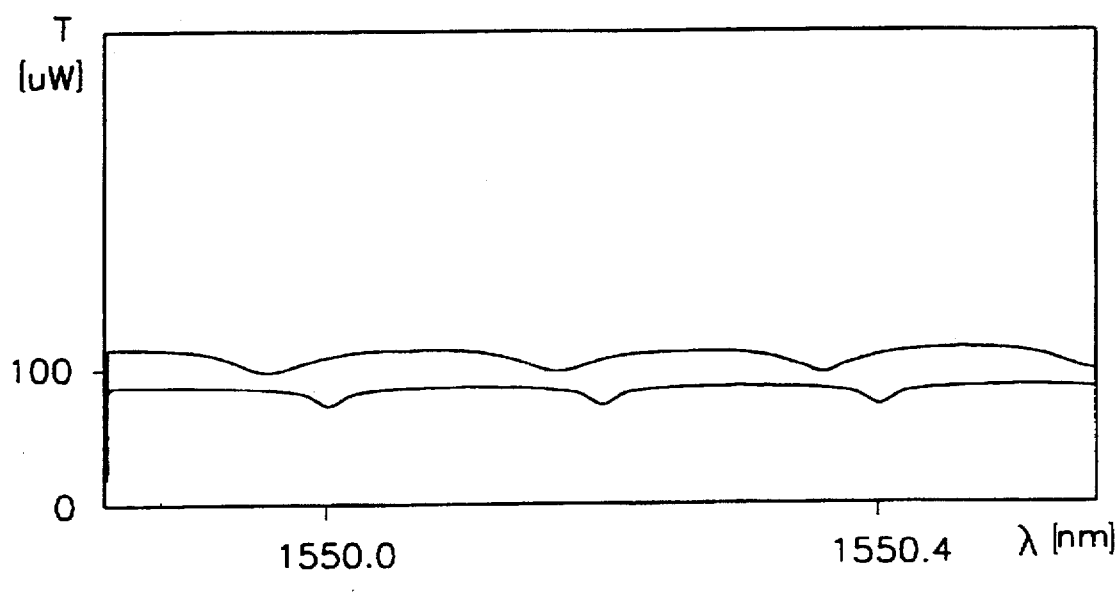

The sample area was then coated with a layer of silicon rubber (Dow Corning) to a thickness of about 10 µm, whereafter transmission curves were produced as in the earlier case. The result is shown in FIG. 9B, in which the uppermost curve was derived from the measuring detector as in the earlier case, and the lowermost curve was derived from the reference detector. As will be seen from the Figure, the measuring detector curve includes clear resonances, which demonstrates that a silicone rubber layer is able to replace the thick LTO-oxide layer on top of the reference ring as cladding.

EXAMPLE 3

The manner in which the ring resonator reacted to non-specific adsorption of bovine serum albumin (BSA) on the surface was investigated by means of an FIA-process (Flow Injection Analysis) with the aid of a ring resonator chip produced and coupled in the same way as in Example 2 and while using a flow cell according to FIG. 4.

A buffer (10 mM Hepes, 0.65M NaCl, 3.4 mM EDTA, 0.05% Tween™ 20) was first applied to the sample surface and the surface was then washed with 50 mM NaOH, whereafter the buffer was replenished. 10 mg/ml BSA (Sigma, USA) in the buffer were then transferred to the sample surface, whereafter the buffer was replenished and the sample surface was again washed with 50 mM NaOH.

Figure 10:
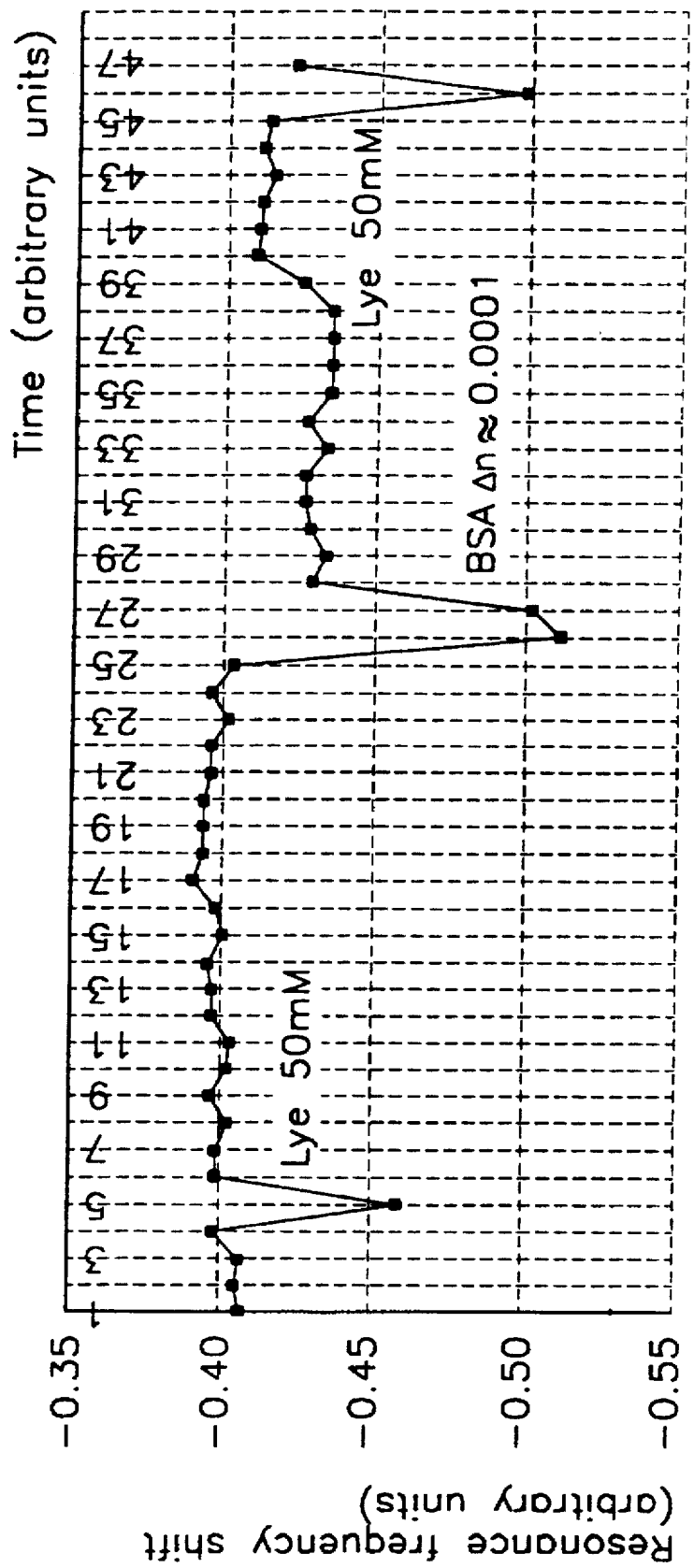
FIG. 10 is a diagram which shows for a ring resonator sensor according to FIG. 1 having a flow cell according to FIG. 4 the resonance frequency shift as a function of time when bovine serum albumin is adsorbed on the sample surface in an FIA-process.

The results are shown in the diagram of FIG. 10, in which the resonance frequency shift (in arbitrary units) is plotted against time (in arbitrary units). It will be seen from the diagram that a large resonance frequency shift occurs when BSA is moved across the sample surface, partly as a result of adsorption of BSA on the surface and partly as a result of the change in bulk concentration. When applying the buffer, a frequency shift will prevail due to adsorbed BSA. The major part of adsorbed BSA is finally washed away with NaOH, and the measuring result will therefore return almost completely to the value that prevailed prior to the BSA-addition.

It will be understood that the invention is not restricted to the aforedescribed and illustrated exemplifying embodiments thereof and that many modifications and changes can be made without departing from the general concept of the invention as it is defined in the following claims.

We claim:

1. A method for determining the refractive index of a gaseous, liquid or solid sample, comprising:
  i) providing a measuring waveguide resonator, which comprises an open waveguide and a closed waveguide, said waveguides being adjacent to each other so as to allow their coupling, and a means for positioning a sample proximal to said closed waveguide so that the presence of said sample can change the effective refractive index of said closed waveguide;
  ii) coupling light from a light source into one end of the open waveguide; and
  iii) measuring the change in the resonance wavelength of said closed waveguide caused by the presence of said sample to determine the refractive index of said gaseous, liquid or solid sample.

2. A method according to claim 1, wherein said light source is a polychromatic light source the light from which is divided spectrally prior to being coupled into the end of said waveguide.

3. A method according to claim 1, wherein said light source is a polychromatic light source the light from which is divided spectrally after being transmitted through the open waveguide.

4. A method according to claim 1, wherein the measuring step (iii) is performed by measuring a shift in the resonance wavelength in relation to the resonance wavelength of a reference waveguide resonator, wherein said reference waveguide resonator comprises an open waveguide, which can be the open waveguide of the measuring waveguide resonator or a separate open waveguide, and a second closed waveguide, said second waveguide being adjacent to said open waveguide so as to allow their coupling.

5. A method according to claim 4, wherein the wavelength of the light emitted from the light source is varied to establish either an absolute or a relative wavelength shift caused by the sample.

6. A method according to claim 5, wherein the light source is a tunable laser.

7. A method according to claim 1, wherein the wavelength of the light emitted from the light source is varied to establish either an absolute or a relative wavelength shift caused by the sample.

8. A method according to claim 7, wherein the light source is a tunable laser.

9. A method according to claim 1, wherein said waveguides are single mode waveguides.

10. A method according to claim 1, wherein said sample is a liquid or gaseous sample.

11. A method for determining the interaction of a solute in a liquid or a gaseous sample with a surface comprising
  i) providing a measuring waveguide resonator, which comprises an open waveguide and a closed waveguide, wherein said closed waveguide comprises a contact area including a surface layer that specifically binds a component of a gaseous or of a liquid sample, thereby changing the refractive index of said surface layer, and wherein said change in refractive index of the surface layer results in a change in the resonance wavelength of the closed waveguide and wherein said closed waveguide is positioned adjacent to said open waveguide so as to couple to said open waveguide;
  ii) coupling light from a light source into one end of the open waveguide; and
  iii) measuring the change in the resonance wavelength of said closed waveguide caused by the presence of said sample to determine the interaction of a solute in said liquid or gaseous sample with said surface layer.

12. A method according to claim 11, wherein said surface layer is derivatized with an antigen, an antibody or with a polynucleotide and wherein said specific binding is an antigen-antibody binding or a nucleic acid hybridization.

13. A method according to claim 11, wherein the measuring step (iii) is performed by measuring a shift in the resonance wavelength in relation to the resonance wavelength of a reference waveguide resonator, wherein said reference waveguide resonator comprises an open waveguide, which can be the open waveguide of the measuring waveguide resonator or a separate open waveguide, and a second closed waveguide, said second waveguide being adjacent to said open waveguide so as to allow their coupling.

14. A method according to claim 13, wherein the wavelength of the light emitted from the light source is varied to establish either an absolute or a relative wavelength shift caused by the sample.

15. A method according to claim 13, wherein the light source is a tunable laser.

16. A method according to claim 11, wherein the wavelength of the light emitted from the light source is varied to establish either an absolute or a relative wavelength shift caused by the sample.

17. A method according to claim 11, wherein the light source is a tunable laser.

18. A method according to claim 11, wherein said waveguides are single mode waveguides.

19. A method according to claim 11, wherein said sample is a liquid or gaseous sample.

20. A method according to claim 11, wherein said light source is a polychromatic light source the light from which is divided spectrally prior to being coupled into the end of said waveguide.

21. A method according to claim 11, wherein said light source is a polychromatic light source the light from which is divided spectrally after being transmitted through the open waveguide.

22. A method for measuring the concentration of a solute in a liquid or gaseous sample, comprising
  i) providing a waveguide resonator, which comprises an open waveguide and a closed waveguide, said waveguides being adjacent to each other so as to allow their coupling, and a means for positioning a sample proximal to said closed waveguide so that the presence of said sample can change the effective refractive index of said closed waveguide;

ii) coupling light from a light source into one end of the open waveguide;

iii) introducing a sample containing said solute into said sample-positioning means;

iv) measuring the resonance wavelength or change in resonance wavelength of said closed waveguide caused by the presence of said sample; and v) determining the concentration of said solute by comparing the resonance wavelength or change in resonance wavelength measured in step iv) to a calibration curve that relates concentration of said solute to said resonance wavelength or change in resonance wavelength.

23. A method according to claim 22, wherein the measuring step (iv) is performed by measuring a shift in the resonance wavelength in relation to the resonance wavelength of a reference waveguide resonator, wherein said reference waveguide resonator comprises an open waveguide, which can be the open waveguide of the measuring waveguide resonator or a separate open waveguide, and a second closed waveguide, said second waveguide being adjacent to said open waveguide so as to allow their coupling.

24. A method according to claim 23, wherein the wavelength of the light emitted from the light source is varied to establish either an absolute or a relative wavelength shift caused by the sample.

25. A method according to claim 23, wherein the light source is a tunable laser.

26. A method according to claim 22, wherein the wavelength of the light emitted from the light source is varied to establish either an absolute or a relative wavelength shift caused by the sample.

27. A method according to claim 22, wherein the light source is a tunable laser.

28. A method according to claim 22, wherein said waveguides are single mode waveguides.

29. A method according to claim 22, wherein said light source is a polychromatic light source the light from which is divided spectrally prior to being coupled into the end of said waveguide.

30. A method according to claim 22, wherein said light source is a polychromatic light source the light from which is divided spectrally after being transmitted through the open waveguide.

31. A method for measuring the concentration of a solute in a liquid or gaseous sample through a surface interaction, comprising i) providing a measuring waveguide resonator, which comprises an open waveguide and a closed waveguide, said waveguides being adjacent to each other so as to allow their coupling, and a means for positioning a sample proximal to said closed waveguide so that the presence of said sample can change the effective refractive index of said closed waveguide;

ii) coupling light from a light source into one end of the open waveguide; and iii) measuring the resonance wavelength of said closed waveguide caused by the presence of said sample;

wherein said closed waveguide comprises a contact area including a surface layer that specifically binds a component of a gaseous or of a liquid sample thereby changing the refractive index of said surface layer, and wherein said change in refractive index of the surface layer results in a change in the resonance wavelength of the closed waveguide; and iv) determining the concentration of said solute by comparing the resonance wavelength or change in resonance wavelength measured in step iii) to a calibration curve that relates concentration of said solute to said resonance wavelength or change in resonance wavelength.

32. A method according to claim 31, wherein said surface layer is derivatized with an antigen, an antibody or with a polynucleotide and wherein said specific binding is an antigen-antibody binding or a nucleic acid hybridization.

33. A method according to claim 31, wherein the measuring step (iii) is performed by measuring a shift in the resonance wavelength in relation to the resonance wavelength of a reference waveguide resonator, wherein said reference waveguide resonator comprises an open waveguide, which can be the open waveguide of the measuring waveguide resonator or a separate open waveguide, and a second closed waveguide, said second waveguide being adjacent to said open waveguide so as to allow their coupling.

34. A method according to claim 33, wherein the wavelength of the light emitted from the light source is varied to establish either an absolute or a relative wavelength shift caused by the sample.

35. A method according to claim 33, wherein the light source is a tunable laser.

36. A method according to claim 31, wherein the wavelength of the light emitted from the light source is varied to establish either an absolute or a relative wavelength shift caused by the sample.

37. A method according to claim 31, wherein the light source is a tunable laser.

38. A method according to claim 31, wherein said waveguides are single mode waveguides.

39. A method according to claim 31, wherein said light source is a polychromatic light source the light from which is divided spectrally prior to being coupled into the end of said waveguide.

40. A method according to claim 31, wherein said light source is a polychromatic light source the light from which is divided spectrally after being transmitted through the open waveguide.

41. A device for measuring the refractive index of a gaseous, liquid or solid sample, comprising a measuring waveguide resonator comprising an open waveguide, a closed waveguide, and a sample positioning means, wherein said closed waveguide is positioned adjacent to said open waveguide so as to couple to said open waveguide and wherein said sample positioning means is operatively connected to said closed waveguide so that the presence of a sample within said sample positioning means can result in a change in the resonance wavelength of said closed waveguide;

a light source;

means for coupling light from said light source into one end of the open waveguide; and means for detecting light transmitted by the open waveguide.

42. A device according to claim 41, wherein said sample positioning means is a flow cell.

43. A device according to claim 41, wherein said sample positioning means comprises a removable sample cell.

44. A device according to claim 41, wherein said sample positioning means is intended for immersion into a gaseous or liquid sample.

45. A device according to claim 41, further comprising a second closed waveguide means for providing a reference waveguide resonator, wherein said second closed waveguide is positioned adjacent to an open waveguide so as to couple to said open waveguide.

46. A device according to claim 41, wherein said reference waveguide resonator further comprises a second open waveguide separate from the open waveguide of a measuring waveguide resonator, and wherein light from said light source is coupled into one open end of each open waveguide.

47. A device according to claim 46, comprising a plurality of measuring waveguide resonators and one reference waveguide resonator, wherein each waveguide resonator has a separate open waveguide arranged in a parallel fashion.

48. A device according to claim 47, wherein a plurality of the sample positioning means include a sample contact area having a surface layer that specifically binds a component of a gaseous or of a liquid sample to change the refractive index of said surface layer, such that the change in refractive index of the surface layer results in a change in the resonance wavelength of the closed waveguide, and wherein said sample contact areas are derivatized with different functionalities to allow the specific binding of several different analytes simultaneously.

49. A device according to claim 41, comprising only one open waveguide and a plurality of closed waveguides positioned along the length of the open waveguide.

50. A device according to claim 49, having at least two measuring waveguide resonators.

51. A device according to claim 50, wherein a plurality of the sample positioning means include a sample contact area having a surface layer that specifically binds a component of a gaseous or of a liquid sample to change the refractive index of said surface layer, such that the change in refractive index of the surface layer results in a change in the resonance wavelength of the closed waveguide, and wherein said sample contact areas are derivatized with different functionalities to allow the specific binding of several different analytes simultaneously.

52. A device according to claim 41, wherein said light source is a polychromatic light source the light from which is divided spectrally prior to being coupled into the end of said open waveguide.

53. A device according to claim 41, wherein said light source is a polychromatic light source the light from which is divided spectrally after being transmitted through the open waveguide.

54. A device according to claim 41, wherein said light source is a tunable laser.

55. A device for measuring a refractive index change carried by binding of a component of a gaseous or liquid sample to a surface layer, comprising a measuring waveguide resonator comprising an open waveguide and a closed waveguide;
wherein said closed waveguide comprises at least one contact area including a surface layer that specifically binds a component of a gaseous or of a liquid sample, thereby changing the refractive index of said surface layer, and wherein said change in refractive index of the surface layer results in a change in the resonance wavelength of the closed waveguide and wherein said closed waveguide is positioned adjacent to said open waveguide so as to couple to said open waveguide;

a light source;
means for coupling light from said light source into one end of the open waveguide; and
means for detecting light transmitted by the open waveguide.

56. A device according to claim 55, wherein said closed waveguide comprises a plurality of sample contact areas and wherein said sample contact areas are derivatized with different functionalities to allow the specific binding of several different analytes simultaneously.

57. A device according to claim 55, wherein said sample positioning means is a flow cell.

58. A device according to claim 55, wherein said sample positioning means comprises a removable sample cell.

59. A device according to claim 55, wherein said sample positioning means is intended for immersion into a gaseous or liquid sample.

60. A device according to claim 55, further comprising a second closed waveguide means for providing a reference waveguide resonator, wherein said second closed waveguide is positioned adjacent to an open waveguide so as to couple to said open waveguide.

61. A device according to claim 55, wherein said reference waveguide resonator further comprises a second open waveguide separate from the open waveguide of a measuring waveguide resonator, and wherein light from said light source is coupled into one open end of each open waveguide.

62. A device according to claim 55, comprising only one open waveguide and a plurality of closed waveguides positioned along the length of the open waveguide.

63. A device according to claim 55, having at least two measuring waveguide resonators.

64. A device according to claim 55, comprising a plurality of measuring waveguide resonators and one reference waveguide resonator, wherein each waveguide resonator has a separate open waveguide arranged in a parallel fashion.

65. A device according to claim 55, wherein said light source is a polychromatic light source the light from which is divided spectrally prior to being coupled into the end of said open waveguide.

66. A device according to claim 55, wherein said light source is a polychromatic light source the light from which is divided spectrally after being transmitted through the open waveguide.

67. A device according to claim 55, wherein said light source is a tunable laser.

68. A method for determining the refractive index of a gaseous, liquid or solid sample, comprising:

i) providing a measuring waveguide resonator, which comprises an open waveguide and a first closed waveguide, said waveguides being adjacent to each other so as to allow their coupling, and a means for positioning a sample proximal to said first closed waveguide so that the presence of said sample can change the effective refractive index of said first closed waveguide;

ii) providing a reference waveguide resonator, which comprises an open waveguide, which can be the open waveguide of the measuring waveguide resonator or a separate open waveguide, and a second closed waveguide, said second waveguide being adjacent to said open waveguide so as to allow their coupling, and wherein said second closed waveguide is of sufficient size as to give rise to a large number of resonances;

iii) coupling light from a tunable laser into one end of the open waveguide of said measuring waveguide resonator and into one end of said reference waveguide resonator;

iv) determining the current-wavelength characteristic of the laser on the basis of variations in the mutual distance between the resonances of the reference waveguide resonator;

v) calibrating the wavelength of the laser on the basis of the current-wavelength characteristic determined in step iv); and vi) measuring the change in the resonance wavelength of the first closed waveguide of said measuring waveguide resonator caused by the presence of said sample.

69. A method for determining the interaction of a solute in a liquid or a gaseous sample with a surface comprising i) providing a measuring waveguide resonator, which comprises an open waveguide and a closed waveguide, said waveguides being adjacent to each other so as to allow their coupling, and a means for positioning a sample proximal to said closed waveguide so that the presence of said sample can change the effective refractive index of said closed waveguide;

ii) providing a reference waveguide resonator, which comprises an open waveguide, which can be the open waveguide of the measuring waveguide resonator or a separate open waveguide, and a second closed waveguide, said second waveguide being adjacent to said open waveguide so as to allow their coupling, and wherein said second closed waveguide is of sufficient size as to give rise to a large number of resonances;

iii) coupling light from a tunable laser into one end of the open waveguide of said measuring waveguide resonator and into one end of said reference waveguide resonator;

iv) determining the current-wavelength characteristic of the laser on the basis of variations in the mutual distance between the resonances of the reference waveguide resonator;

v) calibrating the wavelength of the laser on the basis of the current-wavelength characteristic determined in step iv); and vi) measuring the change in the resonance wavelength of the first closed waveguide of said measuring waveguide resonator caused by the presence of said sample.

70. A method for measuring the concentration of a solute in a liquid or gaseous sample through interaction with a surface, comprising i) providing a waveguide resonator, which comprises an open waveguide and a closed waveguide, wherein said closed waveguide comprises at least one contact area including a surface layer that specifically binds a component of a gaseous or of a liquid sample, thereby changing the refractive index of said surface layer, and wherein said change in refractive index of the surface layer results in a change in the resonance wavelength of the closed waveguide and wherein said closed waveguide is positioned adjacent to said open waveguide so as to couple to said open waveguide;

ii) providing a reference waveguide resonator, which comprises an open waveguide, which can be the open waveguide of the measuring waveguide resonator or a separate open waveguide, and a second closed waveguide, said second waveguide being adjacent to said open waveguide so as to allow their coupling, and wherein said second closed waveguide is of sufficient size as to give rise to a large number of resonances;

iii) coupling light from a tunable laser into one end of the open waveguide of said measuring waveguide resonator and into one end of said reference waveguide resonator;

iv) determining the current-wavelength characteristic of the laser on the basis of variations in the mutual distance between the resonances of the reference waveguide resonator;

v) calibrating the wavelength of the laser on the basis of the current-wavelength characteristic determined in step iv);

vi) measuring the change in the resonance wavelength of the first closed waveguide of said measuring waveguide resonator caused by the presence of said sample; and vii) determining the concentration of said solute by comparing the resonance wavelength change measured in step vi) to a calibration curve that relates concentration of said solute to said change in resonance wavelength.

71. A method for measuring concentration of a solute in a liquid or gaseous sample, comprising i) providing a measuring waveguide resonator, which comprises an open waveguide and a closed waveguide, said waveguides being adjacent to each other so as to allow their coupling, and a means for positioning a sample proximal to said closed waveguide so that the presence of said sample can change the effective refractive index of said closed waveguide;

ii) providing a reference waveguide resonator, which comprises an open waveguide, which can be the open waveguide of the measuring waveguide resonator or a separate open waveguide, and a second closed waveguide, said second waveguide being adjacent to said open waveguide so as to allow their coupling, and wherein said second closed waveguide is of sufficient size as to give rise to a large number of resonances;

iii) coupling light from a tunable laser into one end of the open waveguide of said measuring waveguide resonator and into one end of said reference waveguide resonator;

iv) determining the current-wavelength characteristic of the laser on the basis of variations in the mutual distance between the resonances of the reference waveguide resonator;

v) calibrating the wavelength of the laser on the basis of the current-wavelength characteristic determined in step iv);

vi) measuring the change in the resonance wavelength of the first closed waveguide of said measuring waveguide resonator caused by the presence of said sample; and vii) determining the concentration of said solute by comparing the resonance wavelength change measured in step vi) to a calibration curve that relates concentration of said solute to said change in resonance wavelength.

* * * * *